(12) United States Patent
Pascolo (10) Patent No.: US 10,980,875 B2
(45) Date of Patent: Apr. 20, 2021

(54) CYTOTOXIC IMMUNOSTIMULATING PARTICLES AND USES THEREOF

(71) Applicant: BIONTECH AG, Mainz (DE)

(72) Inventor: Steve Pascolo, Zürich (CH)

(73) Assignee: BIONTECH AG, Mainz (DE)

( * ) Notice: Subject to any disclaimer, the term of this patent is extended or adjusted under 35 U.S.C. 154(b) by 146 days.

(21) Appl. No.: 15/763,541

(22) PCT Filed: Oct. 20, 2016

(86) PCT No.: PCT/EP2016/075146
§ 371 (c)(1),
(2) Date: Mar. 27, 2018

(87) PCT Pub. No.: WO2017/068013
PCT Pub. Date: Apr. 27, 2017

(65) Prior Publication Data
US 2018/0289797 A1    Oct. 11, 2018

(30) Foreign Application Priority Data

Oct. 21, 2015   (WO) ................. PCT/EP2015/074386

(51) Int. Cl.
*A61K 39/39*      (2006.01)
*A61K 39/00*      (2006.01)

(52) U.S. Cl.
CPC .......... *A61K 39/39* (2013.01); *A61K 2039/53* (2013.01); *A61K 2039/55555* (2013.01); *A61K 2039/572* (2013.01)

(58) Field of Classification Search
CPC ...................................................... A61K 39/39
See application file for complete search history.

(56) References Cited

U.S. PATENT DOCUMENTS

| 5,614,505 A | * | 3/1997 | Gmeiner | ................ | C07H 21/00 514/50 |
| 2011/0123637 A1 | | 5/2011 | Pascolo et al. | | |
| 2012/0258046 A1 | * | 10/2012 | Mutzke | ................... | A61P 37/04 424/9.1 |

FOREIGN PATENT DOCUMENTS

| WO | WO 2009/046739 | 4/2009 |
| WO | WO 2009/088401 | 7/2009 |
| WO | WO 2009/144230 | 12/2009 |
| WO | WO 2011/005799 | 1/2011 |

OTHER PUBLICATIONS

Meyer et al (Molecular Pharmaceutics. 2009; 6(3): 752-762). (Year: 2009).*
Plasay (Journal of Chemical and Pharmaceutical Sciences. Dec. 2016; 9(4): 2674-2676). (Year: 2016).*
Diessner et al. (Cell Death and Disease (2014) 5, e1149; doi: 10.1038/cddis.2014.115). (Year: 2014).*
DeLong et al. (Biomaterials. Nov. 2009 ; 30(32): 6451-6459). (Year: 2009).*
Barh et al. (Curr Oncol. Feb. 2010; 17(1): 70-80) (Year: 2010).*
Jafari et al. (Current Medicinal Chemistry, 2012, 19, 197-208) (Year: 2012).*
International Search Report (ISR) for PCT/EP2016/075146 dated Dec. 13, 2016, pp. 1-4.
Written Opinion of the International Searching Authority for PCT/EP2016/075146 dated Dec. 13, 2016, pp. 1-5.
Nakamura, Kazuya et al. "A Double-modulation Strategy in Cancer Treatment With a Chemotherapeutic Agent and siRNA" Molecular Therapy (2011) vol. 19(1), pp. 2040-2047.
Zhang, Yuan et al. "Combinational delivery of c-myc siRNA and nucleoside analogs in a single, synthetic nanocarrier for targeted cancer therapy" Biomaterials (2013) vol. 34, pp. 8459-8468.
Mayer et al., "Oligonucleotide-protamine-albumin nanoparticles: Protamine sulfate causes drastic size reduction" Journal of Controlled Release, 106(1-2):181-87 (Aug. 2005).
Ahern, "Biochemical, Reagent Kits Offer Scientists Good Return on Investment" The Scientist, pp. 20-22, (Jul. 1995).
Bourquin et al., Systemic Cancer Therapy with a Small Molecule Agonist of Toll-like Receptor 7 Can Be Improved by Circumventing TLR Tolerance Cancer Res. 71:5123-33 (2011).
Kerkmann et al., "Immunostimulatory Properties of CpG-Oligonucleotides Are Enhanced by the Use of Protamine Nanoparticles" Oligonucleotides 16:313-22 (2006).
Makowska et al., "Sequential Induction of type I and II Interferons mediates a long-lasting gene induction in the liver in response to a novel toll-like receptor 9 agonist" Journal of Hepatology 48:743-49 (2013).
Rettig et al., "Particle Size and activation threshold:a new dimension of danger signaling" Blood 115(22):4533-41 (Jun. 2010).
Shima et al., "Synergistic Stimulation of Antigen Presenting Cells via TLR by Combining CpG ODN and Poly (y-glutamic acid)-Based Nanoparticles as Vaccine Adjuvants" Bioconjugate Chemistry 24:926-33 (2013).
Zhang et al., "Structural Analyses of Toll-like Receptor 7 Reveal Detailed RNA Sequence Specificity and Recognition Mechanism of Agonistic Ligands" Cell Reports 25:3371-81 (Dec. 2018).
U.S. Appl. No. 15/763,601, filed Mar. 27, 2018, Methods and Means for Inducing an Immune Response, US 2018-0318436, pending.
U.S. Appl. No. 15/763,601, filed Mar. 27, 2018, Biontech AG.

*Primary Examiner* — Scott Long
(74) *Attorney, Agent, or Firm* — McDonnell Boehnen Hulbert & Bergoff LLP (57) ABSTRACT

The present invention relates to particles comprising RNA, in which the RNA is associated with a cationic polymer or lipid or with both a cationic polymer and lipid, wherein the RNA comprises a cytotoxic nucleotide or cytotoxic nucleotide analog and/or the RNA is covalently attached to a cytotoxin, pharmaceutical compositions containing said particles and pharmaceutical uses of the particles and pharmaceutical compositions. The particles of the present invention are particularly useful as an immunostimulating medicament capable to block proliferation or induce death in dividing cells such as tumor cells.

13 Claims, 4 Drawing Sheets
Specification includes a Sequence Listing.

Figure 1

Average Diameter: 107.308 nm

CYTOTOXIC IMMUNOSTIMULATING PARTICLES AND USES THEREOF

CROSS-REFERENCE TO RELATED APPLICATION

This application is a U.S. national phase of International Application No. PCT/EP2016/075146, filed on Oct. 20, 2016, which claims priority to International Application No. PCT/EP2015/074386, filed Oct. 21, 2015, both of which are incorporated by reference herein in their entirety.

The present invention relates to immunomodulating cytotoxic particles comprising immunostimulating RNA comprising a cytotoxic nucleotide or cytotoxic nucleotide analog and/or being covalently attached to a cytotoxin (modified toxic immunostimulating RNA; mtiRNA) and a cationic polymer and/or lipid, pharmaceutical compositions comprising said particles and pharmaceutical uses of the particles and pharmaceutical compositions. The particles of the present invention are particularly useful as anticancer medicament with dual biological activities: immunostimulation and chemotherapeutic anti-cancer effect.

BACKGROUND OF THE INVENTION

Exogenous RNA is a danger signal that can trigger immune sensors of infections, such as Toll-Like Receptors (TLRs) 3, 7 and 8 located in endosomes or RIG-I located in cytosol. To exert its immunostimulatinng activity, exogenous RNA must be formulated for example in particles such as Protamine-RNA nanoparticles (Rettig L. et al., 2010, Blood 115(22):4533-41 and WO 2009/144230 A1).

Modified toxic purines or pyrimidines (eventually attached to a sugar connected or not to a phosphate) are a group of anti-cancer drugs belonging to the family of metabolite analogs. Once in cells they interfere with the metabolism of nucleic acids (e.g. synthesis of A, C, G, T or U, and/or replication of DNA, and/or production of RNA). Thereby, they induce cell death, particularly in quickly dividing cells such as tumor cells.

The present invention is based on the observation that the introduction of modified bases or nucleosides or nucleotides that can induce cell death into the RNA of immunostimulating RNA particles results in particles having immunostimulatory and cytotoxic effects. As alternative or in addition, a toxic moiety can be attached to the RNA. Such RNA will be called mtiRNA for "modified toxic immunostimulating RNA". In particular, it was observed that RNA containing at least one anti-cancer base analog can be formulated in particles, generating nanoparticles of a defined size from an average of 50 nm to 990 nm (depending on the precise conditions of formulation as described in WO 2009/144230 A1) and that these particles have a dual activity of immunostimulation in blood cells and cytotoxicity on tumor cells.

SUMMARY OF THE INVENTION

In a first aspect, the present invention relates to a particle comprising RNA, in which the RNA is associated with a cationic polymer or lipid or with both a cationic polymer and lipid, wherein the RNA comprises a cytotoxic nucleotide or cytotoxic nucleotide analog and/or the RNA is covalently attached to a cytotoxin.

In one embodiment, the RNA comprises at least one U nucleotide, at least one G nucleotide, at least one modified U nucleotide, at least one modified G nucleotide, or a combination thereof. In one embodiment, the at least one modified U nucleotide and/or the at least one modified G nucleotide is a cytotoxic nucleotide or cytotoxic nucleotide analog.

In one embodiment, the cytotoxic nucleotide or cytotoxic nucleotide analog comprises a moiety selected from the group consisting of azacitidine, capecitabine, cladribine, clofarabine, cytarabine, decitabine, floxuridine, fludarabine, fluorouridine, gemcitabine, nelarabine, pentostatin, and a nucleotide comprising a base selected from the group consisting of azathioprine, carmofur, mercaptopurine, tegafur, and tioguanine.

In one embodiment, the cytotoxin is selected from the group consisting of an alkylating agent, a cyanide group, an antimetabolite, an antimicrotubule agent, a topoisomerase inhibitor, a tyrosine kinase inhibitor, and a cytotoxic antigen-specific structure such as a cytotoxic antibody. In one embodiment, the cytotoxic antibody is selected from the group consisting of alemtuzumab, bevacizumab, cetuximab, denosumab, gemtuzumab ozogamicin, ibritumomab tiuxetan, ipilimumab, ofatumumab, panitumumab, pertuzumab, rituximab, tositumomab, and trastuzumab.

In one embodiment, the cytotoxin is selected from the group consisting of methotrexate, pemetrexed, raltitrexed, hydroxycarbamide, irinotecan, topotecan, daunorubicin, doxorubicin, epirubicin, idarubicin, mitoxantrone, valrubicin, etoposide, teniposide, cabazitaxel, docetaxel, paclitaxel, vinblastine, vincristine, vindesine, vinflunine, vinorelbine, amsacrine, bendamustine, busulfan, carmustine, chlorambucil, chlormethine, cyclophosphamide, dacarbazine, fotemustine, ifosfamide, lomustine, mechlorethamine, melphalan, mitozolomide, streptozotocin, temozolomide, thiotepa, uramustine, carboplatin, cisplatin, nedaplatin, oxaliplatin, altretamine, bleomycin, bortezomib, dactinomycin, estramustine, ixabepilone, mitomycin, procarbazine, satraplatin, triplatin tetranitrate, afatinib, aflibercept, axitinib, bosutinib, crizotinib, dasatinib, erlotinib, gefitinib, imatinib, lapatinib, nilotinib, pazopanib, ponatinib, regorafenib, ruxolitinib, sorafenib, sunitinib, vandetanib, everolimus, temsirolimus, alitretinoin, bexarotene, isotretinoin, tamibarotene, tretinoin, lenalidomide, pomalidomide, thalidomide, romidepsin, valproate, vorinostat, anagrelide, arsenic trioxide, asparaginase, denileukin diftitox, and vemurafenib.

In one embodiment, the RNA is an oligonucleotide or is a messenger RNA (mRNA). In one embodiment, the RNA is an oligonucleotide of from 6 to 100 nucleotides, preferably an oligonucleotide having the sequence according to SEQ ID NO: 1. In one embodiment, the RNA is an mRNA of from 50 to 10,000 nucleotides.

In one embodiment, the cationic polymer is selected from the group consisting of Protamine, polyethyleneimine, poly-L-lysine, poly-L-arginine and histone.

In one embodiment, the particle of the invention comprises RNA and Protamine. In one embodiment, the Protamine-RNA particle is a Protamine-RNA nanoparticle having a size in the range from about 10 nm to about 990 nm, from about 10 nm to about 750 nm, from about 10 nm to about 450 nm, from about 50 nm to about 450 nm, from about 50 nm to about 100 nm, or from about 90 nm to about 110 nm. In one embodiment, the Protamine-RNA nanoparticle has a Protamin:RNA mass ratio in the range from about 16:1 to about 1:2, from about 8:1 to about 1:2, or from about 4:1 to about 1:2.

In one embodiment, the RNA, when transfected into cells or when taken up by cells, induces an immune response and/or induces cytotoxicity. In one embodiment, particles of the invention when contacted with appropriate cells or administered to a subject are capable of inducing cytokines, preferably type I interferons such as interferon-alpha, and inducing cell death of preferably targeted cells (for example rapidly dividing tumor cells). The induction of the immune system preferably involves the stimulation of one or more of TLR-7, TLR-8 and TLR-3, preferably TLR-7 and TLR-8, more preferably TLR-7, TLR-8 and TLR-3.

In another aspect, the present invention relates to a pharmaceutical composition comprising the particle of the invention, and a pharmaceutically acceptable carrier. In one embodiment, the pharmaceutical composition further comprises an antigen and/or an adjuvant. The pharmaceutical composition of the invention may optionally comprise at least one diluent and/or excipient. The pharmaceutical composition of the invention may further comprise at least one adjuvant and/or at least one antigen.

The pharmaceutical composition of the present invention may be co-administered with a further immunomodulating agent which may be selected from the group consisting of chemotherapeutic drugs, chloroquine, anti-CTLA-4, anti-PD1, anti-PDL1 or anti-regulatory T-cell reagents and/or at least one antigen. The immunomodulating agent and/or the at least one antigen may be administered prior to, simultaneously with or after administration of the pharmaceutical composition of the present invention. If the immunomodulating agent and/or the at least one antigen is administered simultaneously with administration of the pharmaceutical composition of the present invention, the immunomodulating agent and/or the at least one antigen may be comprised in the pharmaceutical composition of the present invention.

In another aspect, the present invention relates to the pharmaceutical composition of the invention for use as a medicament.

In another aspect, the present invention relates to the pharmaceutical composition of the invention for use in inducing an immune response and/or for use in inducing cytotoxicity.

In another aspect, the present invention relates to the pharmaceutical composition of the invention for use in therapy. In one embodiment, the therapy comprises inducing an immune response and/or inducing cytotoxicity. In one embodiment, the therapy is treating or preventing cancer.

In another aspect, the present invention relates to a method for inducing an immune response and/or for inducing cytotoxicity in a subject comprising administering the pharmaceutical composition of the invention to the subject.

In another aspect, the present invention relates to a therapeutic method comprising administering the pharmaceutical composition of the invention to a subject. In one embodiment, the therapy comprises inducing an immune response and/or inducing cytotoxicity. In one embodiment, the therapy is treating or preventing cancer.

BRIEF DESCRIPTION OF THE DRAWINGS

Other objects, advantages and novel features of the present invention will become apparent from the following detailed description when considered in conjunction with the accompanying drawings. "Complete medium" means RPMI containing 10% Foetal Calf Serum and antibiotics (penicillin&streptomycin) and L-glutamine.

FIG. 1: A modified toxic immunostimulating RNA oligonucleotide can be formulated with Protamine in particles A modified toxic immunostimulating RNA (mtiRNA) oligonucleotide of 21 residues with the sequence 5' A.G.U (5F).G.U(5F).U(5F).A.U(5F).U(5F).C.U(5F).U(5F).G.U (5F).A.U(5F).G.G.U(5F). U(5F).G 3' where U(5F) is 5 fluoro Uridine was synthesized (Dharmacon, Belgium), desalted and lyophilized. It was resuspended in pure water at 1 mg/ml. 120 micrograms of mtiRNA (120 microliters) were diluted with 120 microliters of water to reach a RNA final concentration of 0.5 mg/ml. Protamine 5000 IPEX for injection was diluted to 0.5 mg/ml in water. 240 microliters of mtiRNA (120 micrograms) and 240 microliters of diluted Protamine (120 micrograms) were mixed together and the solution was homogenized by pipetting up and down. After 10 minutes, Glucose 40% was added to provide a solution at 5% Glucose and 5% Glucose was added to get a final concentration of RNA (and of Protamine) of 10 micrograms in 100 microliters. 30 microliters of this solution were diluted with 170 microliters of Glucose 5% and analysed by light scattering spectroscopy using a DynaPro PlateREader-II (Wyatt Technology). The results presented in FIG. 1 demonstrate that the mtiRNA can be formulated in homogenous Protamine particles whereby the particles have the expected size (observed previously using non modified RNA formulated in identical conditions) of approximately 107 nm in average. Thus the toxic modification (5 fluoro Uridine) does not interfere with the capacity of Protamine to condensate the nucleic acid in homogenous particles of a defined size.

CT26 tumor cells were plated in a 48 well plate at 5000 cells per well in 200 microliters of complete medium. Plates were put at 37° C. over night. Then, medium was eliminated by reverting the plate and 200 microliters of fresh complete medium containing titrating amounts of Protamine-mtiRNA particles ("PR11_5FU_Oligo") or Protamine-RNA ("PR11_Unmod(R18)_oligo") were added (Protamine-mtiRNA and Protamine-RNA particles of 100 nm were prepared by mixing 30 micrograms of mtiRNA (5' A.G.U (5F).G.U(5F).U(5F).A.U(5F).U(5F).C.U(5F).U(5F).G.U (5F).A.U(5F).G.G.U(5F). U(5F).G 3' where U(5F) is 5 fluoro Uridine) or unmodified RNA oligo (sequence 5' AGUGUUAUUCUUGUAUGG 3') at 0.5 mg/ml in pure water with 30 micrograms of Protamine at 0.5 mg/ml in pure water). Cells were incubated 2.5 hours at 37° C. Then, medium was eliminated by reverting the plate and 800 microliters of fresh complete medium was added in each well. The plate was put at 37° C. for three days. Then, medium was eliminated by reverting the plate, 500 microliters of RPM were added in each well for wash, the plate was reverted to eliminate RPMI and 500 microliters of PBS were added in each well. Then, the plate was frozen at −80° C. One day later, the plate was let at room temperature 4 hours and span 5 minutes at 1500 rpm. 10 microliters of supernatant from each well was put in the wells of a 96 well plate with flat bottom. 40 microliters of LDH substrate (Cytotox96 kit, Promega) was added in each well. After approximately 5 minutes, 40 microliters of stop solution was added in each well and OD490 nm was recorded. FIG. 2 presents the results of triplicates (OD490 nm value of sample−OD490 nm value obtained for 10 microliters PBS+ 40 microliters LDH substrate+40 microliters stop solution). They demonstrate that while Protamine-RNA particles do not interfere with cell proliferation, Protamine-mtiRNA particles at more than 0.625 microgram/ml (related to RNA concentration in the cell culture) pulsed 2.5 hours blocks cell proliferation. Thus Protamine-mtiRNA particles are toxic to tumor cells.

Protamine-mtiRNA ("PR_5FU") and Protamine-mRNA (Luciferase) ("PR_Luc") particles were prepared as in FIG. 2 (Protamine-mtiRNA and Protamine-mRNA particles of 100 nm were prepared by mixing 30 micrograms of mtiRNA 5' A.G.U(5F).G.U(5F).U(5F).A.U(5F).U(5F).C.U(5F).U (5F).G.U(5F).A.U(5F).G.G.U(5F). U(5F).G 3' where U(5F) is 5 fluoro Uridine or unmodified luciferase coding mRNA at 0.5 mg/ml in pure water with 30 micrograms of Protamine at 0.5 mg/ml in pure water). 4 microliters of particles were put in a well of a 96 well plate with U bottom. Two hundred microliters (1 million of cells) of a fresh human Peripheral Blood Mononuclear Cells (PBMCs obtained by centrifugation of fresh blood on a ficol solution) preparation were added on top of particles. The plate was incubated over night at 37° C. As negative control, PBMCs were cultured alone ("PBMCs alone") or with 1 microgram of Protamine ("Protamine") or with 1 microgram of mtiRNA ("5FU"). Then, supernatants were collected and interferon-alpha was quantified using pan-interferon-alpha ELISA kit from PBL. The results presented in FIG. 3 demonstrate that similarly to Protamine-mRNA (luciferase) particles, Protamine-mtiRNA particles are immunostimulating, inducing interferon-alpha production in PBMCs. Thus, the 5 fluoro Uridine residues in the mtiRNA oligonucleotide do not interfere with the capacity of the particles to stimulate human immune cells including plasmacytoid dendritic cells.

Protamine-mtiRNA particles were prepared as in FIG. 1 by mixing 120 micrograms of mtiRNA (5' A.G.U(5F).G.U (5F).U(5F).A.U(5F).U(5F).C.U(5F).U(5F).G.U(5F).A.U (5F).G.G.U(5F). U(5F).G 3' where U(5F) is 5 fluoro Uridine) at 0.5 mg/ml in pure water with 120 micrograms of Protamine at 0.5 mg/ml in pure water. After 10 minutes, glucose 40% was added to provide a solution at 5% Glucose and 5% glucose was further added to have a solution that contains 10 micrograms mtiRNA in 100 microliters. Five BALB/c mice were injected intravenous with 100 microliters of the solution and reinjected two hours later again with 100 microliters of the Protamine-mtiRNA formulation ("PR11_5FU"). As controls 4 mice received two injections (two hours apart) of 5% Glucose ("Untreated"). Serum was collected from peripheral blood 3 hours after the second injection. Interferon-alpha in 20 microliters of serum was quantified using Verikine™ ELISA kit from PBL. The results presented in FIG. 4 demonstrate that the Protamine-mtiRNA particles can induce immunostimulation (production of interferon-alpha) in vivo. Thus, the 5 fluoro Uridine residues in the mtiRNA oligonucleotide do not interfere with the capacity of the particles to stimulate mouse immune cells in vivo.

DETAILED DESCRIPTION OF THE INVENTION

Figure 1:
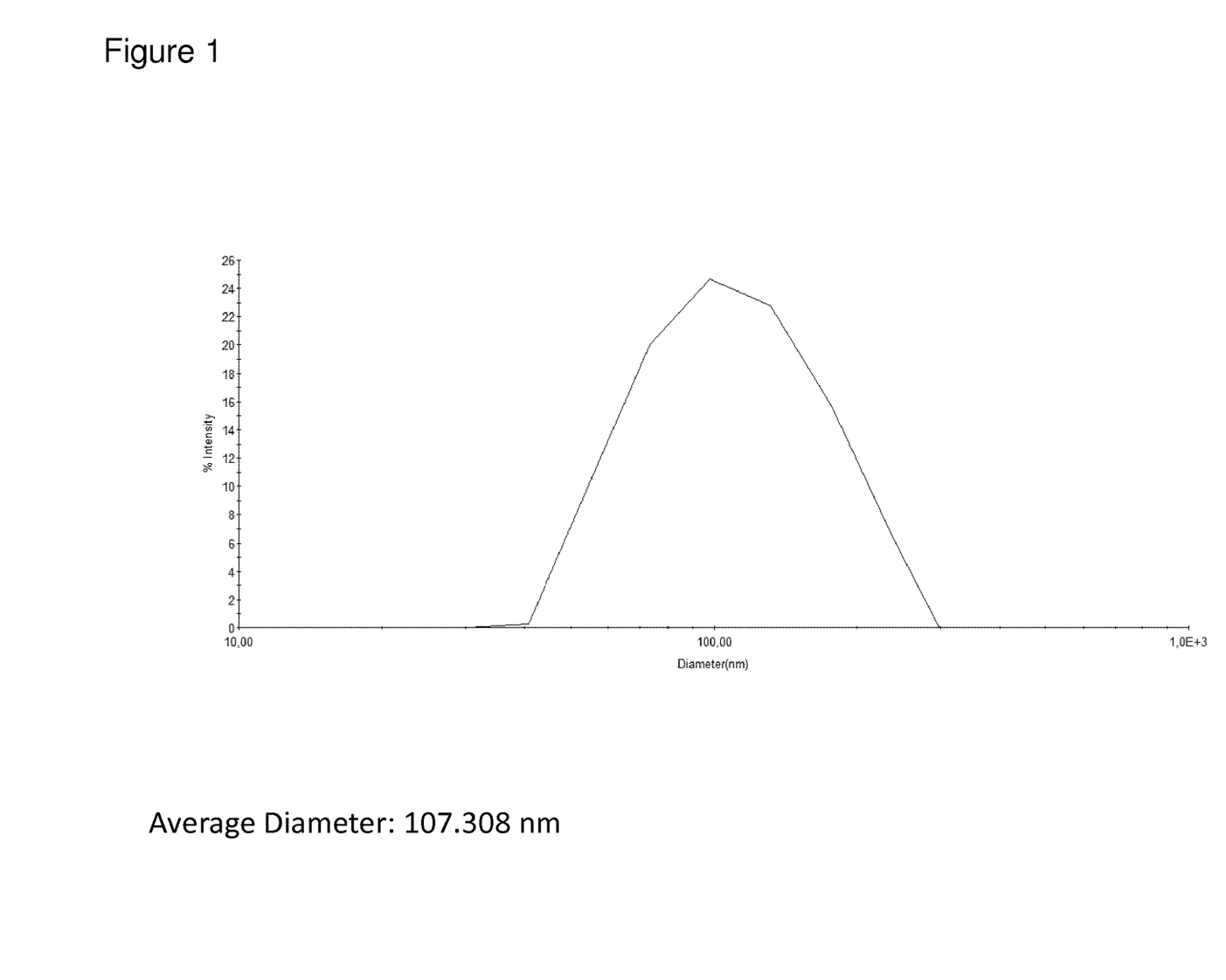
Figure 2:
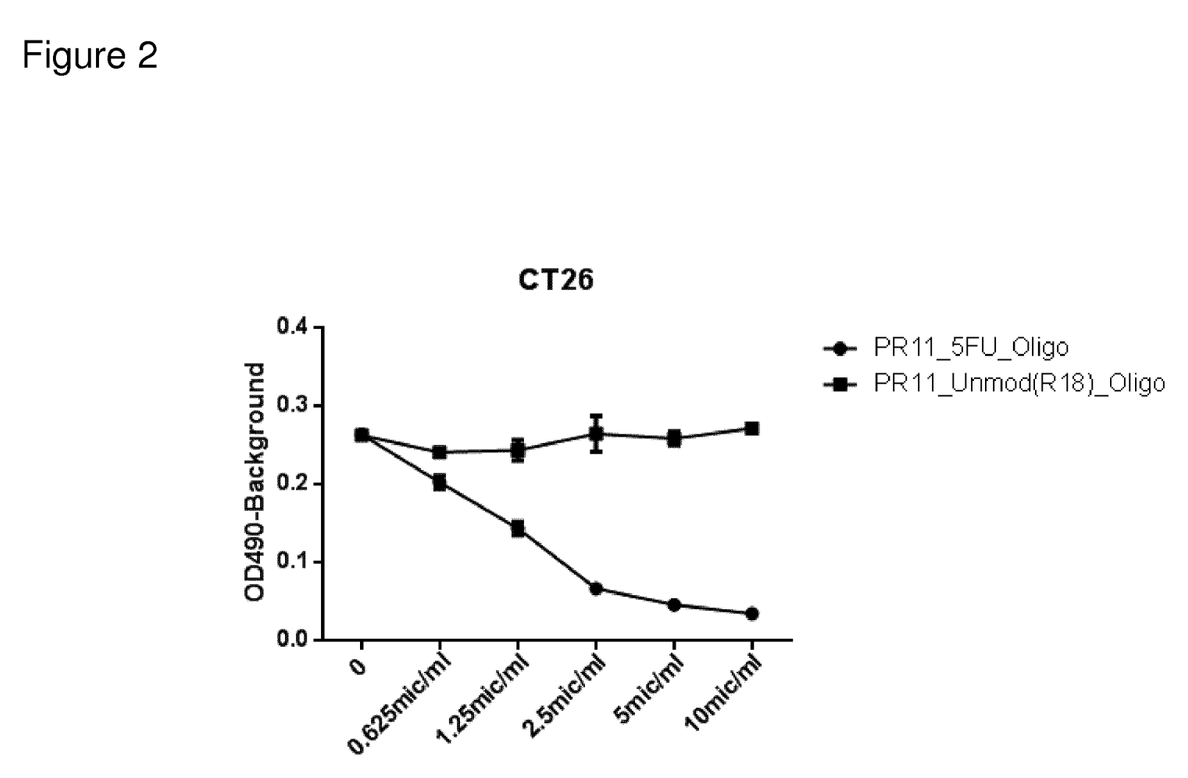
FIG. 2: Protamine-mtiRNA particles are toxic to tumor cells
Figure 3:
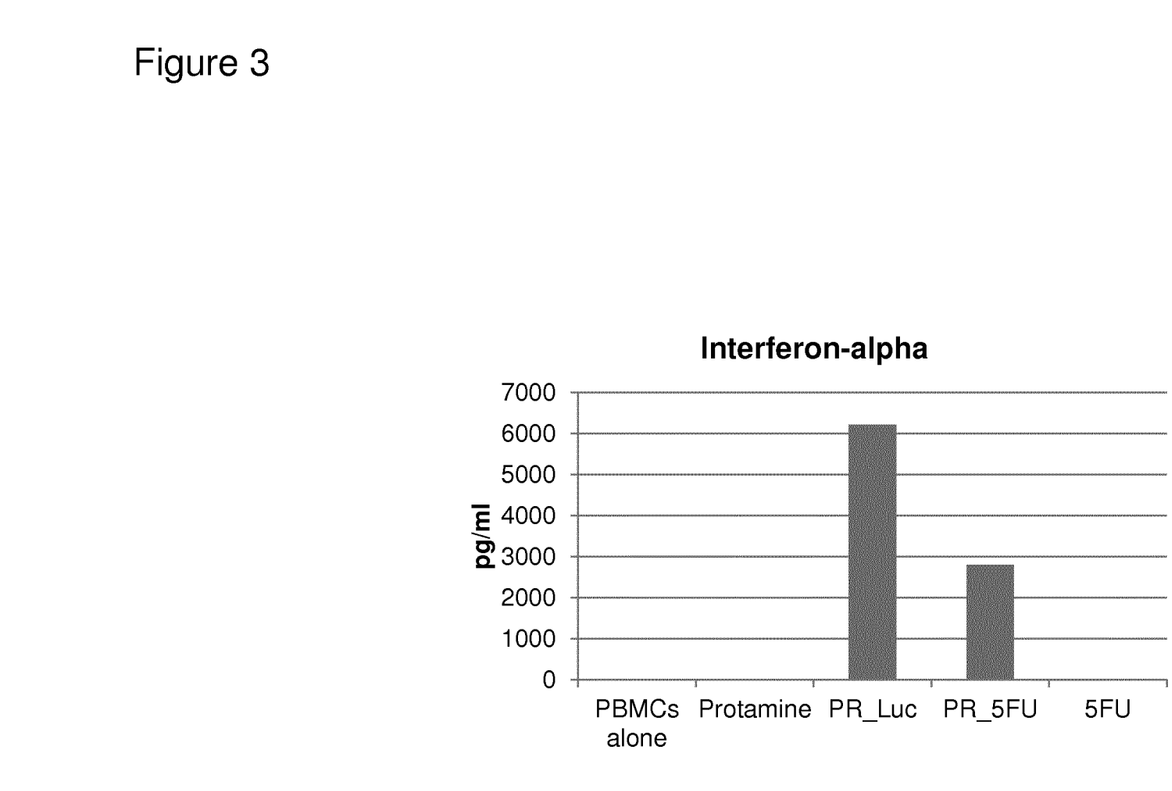
FIG. 3: Protamine-mtiRNA particles are immunostimulating in vitro
Figure 4:
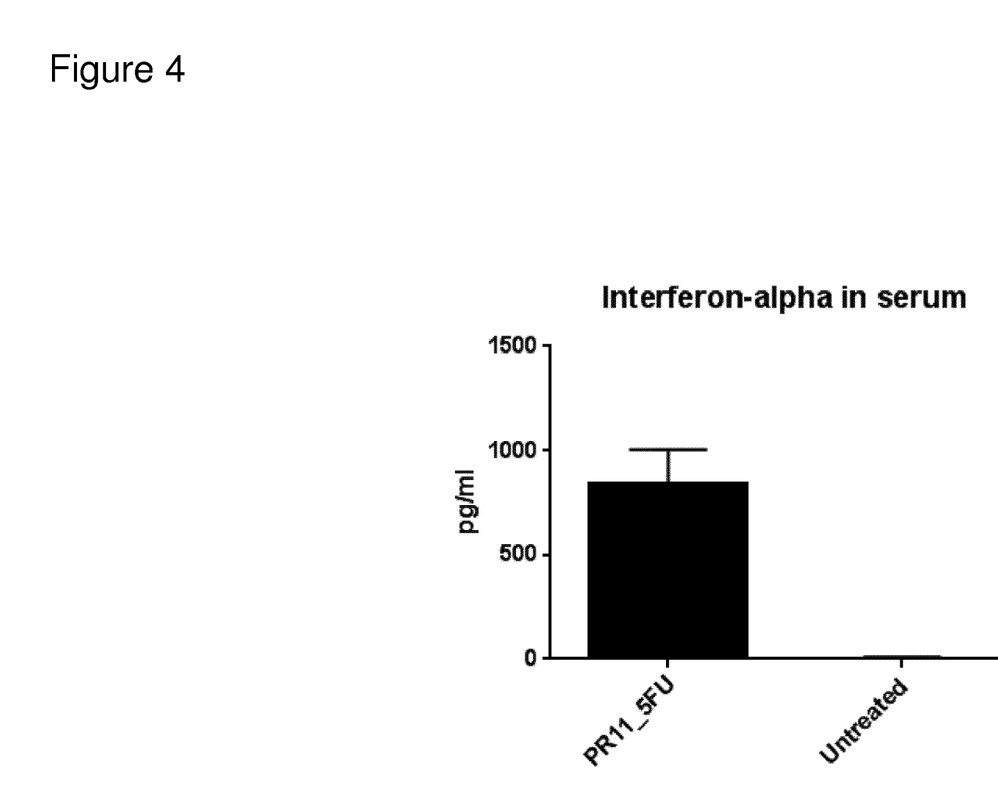
FIG. 4: Protamine-mtiRNA particles are immunostimulating in vivo

In the following, definitions will be provided which apply to all aspects of the present invention.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual, 2$^{nd}$ Edition*, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present inventor surprisingly observed that particles containing a modified RNA containing cytotoxic moieties (e.g. 5-fluorouridine) have a double biological activity: stimulation of immune cells and toxicity for diseased cells such as tumor cells. For generating such toxic immunostimulating particles the modified toxic immunostimulating RNA (mtiRNA) is preferably immunostimulating RNA (preferably comprising U-residues and/or G residues) comprising one or more toxic moieties which can be a modification on the RNA residues or a toxic cargo (e.g. a toxin). Furthermore, Protamine is preferred as cationic carrier agent (cationic polymer) in the particles and the mass ratio of Protamine to RNA (mtiRNA and any other RNA which may optionally be comprised by the particles of the invention) is preferably at least 0.5 (preferably not more than twice more RNA than Protamine). In preferred embodiments this ratio is 1 or higher (most preferred the same mass amount of Protamine and RNA or more Protamine than total RNA is used), 2 or higher, 4 or higher and preferably up to 16, more preferably up to 8. In one embodiment, the Protamine:RNA weight ratio is from 16:1 to 1:2, more preferably from 4:1 to 1:2. A mass ratio of Protamine to RNA of 1 to 1 or higher (i.e. more Protamine than total RNA) is preferred since it results in an optimal compaction of RNA.

A preferred procedure for the preparation of particles of the invention containing Protamine as the cationic agent (cationic polymer) comprises the steps of diluting Protamine and RNA (including mtiRNA and optionally any other RNA such as non-modified RNA) at concentrations of less than approx. 5 mg/ml, at best at 1 mg/ml or less using pure water or low salt solution (preferably less than 125 mM electrolytes), and then mixing the two solutions.

In one embodiment, particles of the present invention are prepared by a method comprising the following steps:
(a) providing an aqueous solution of RNA;
(b) providing an aqueous solution of Protamine; and
(c) combining the solutions obtained in steps (a) and (b).

Preferably, the above step (a) is performed by resuspending an appropriate amount of dried RNA in an aqueous solution containing 0 to 125 mM electrolytes, preferably containing less than 100 mM, more preferably less than 50 mM and, in particular, less than 25 mM electrolytes.

Preferably, the above step (b) is carried out by diluting a solution of Protamine, preferably an aqueous isotonic stock solution of Protamine, preferably containing 1000 ("Protamine 1000") to 5000 ("Protamine 5000") heparin-neutralizing units per ml with a solution containing 0 to 125 mM electrolytes, preferably containing less than 100 mM, more preferably less than 50 mM and, in particular, less than 25 mM electrolytes. For example, Protamine 1000 and 5000 stock solutions are commercially available from Valeant Pharmaceuticals International, Aliso Viejo, Calif., USA, under the trademarks Valeant® 1000 and 5000, respectively.

In one embodiment, particles of the present invention are prepared by diluting Protamine and RNA to less than 5 mg/ml, preferably to 1 mg/ml or less in an aqueous solution containing 0 to 125 mM electrolytes, preferably in pure water. In one embodiment, (i) Protamine is formulated as a 0.5 mg/ml solution by diluting a pharmaceutical isotonic solution of at least 10 mg/ml (Protamine 5000) with pure water and (ii) RNA is formulated as a 0.5 mg/ml solution by diluting dried RNA pellets in pure water and (iii) these two preparations are mixed. It has been demonstrated according to the invention that such procedure forms homogenous particles of defined size.

In one embodiment, particles of the present invention are prepared by a method comprising the following steps:
(a) providing an aqueous solution of RNA at less than 5 mg/ml in pure water;
(b) providing an aqueous solution of Protamine at less than 5 mg/ml by diluting an aqueous isotonic stock solution containing 5000 heparin-neutralizing units of Protamine per ml with pure water;
(c) combining the solutions obtained in steps (a) and (b).

The term "immune response" refers to a response within an organism that preferably protects against disease. An immune response may be prophylactic and/or therapeutic. According to the invention an "induced immune response" may be reflected by an increased level of interferon-alpha.

The term "immunogenicity" refers to the ability of a particular substance, in particular RNA, to provoke an immune response in the body of an animal such as a human. In other words, immunogenicity is the ability to induce an immune response.

"Inducing an immune response" may mean that there was no immune response before inducing an immune response, but it may also mean that there was a certain level of immune response before inducing an immune response and after inducing an immune response said immune response is enhanced. Thus, "inducing an immune response" includes "enhancing an immune response". Preferably, after inducing an immune response in a subject, said subject is protected from developing a disease such as a cancer disease or the disease condition is ameliorated by inducing an immune response.

The term "cytotoxic" refers to the ability of a particular substance, in particular RNA, of being detrimental, in particular toxic to cells. In one embodiment, such substance kills cells. Treating cells with a cytotoxic compound can result in a variety of cell fates. The cells may undergo necrosis, in which they lose membrane integrity and die rapidly as a result of cell lysis, the cells can stop actively growing and dividing (a decrease in cell viability), or the cells can activate a genetic program of controlled cell death (apoptosis).

"Inducing cytotoxicity" may mean that there was no cytotoxicity before inducing cytotoxicity, but it may also mean that there was a certain level of cytotoxicity before inducing cytotoxicity and after inducing cytotoxicity said cytotoxicity is enhanced.

Thus, "inducing cytotoxicity" includes "enhancing cytotoxicity". Preferably, after inducing cytotoxicity in a subject, said subject is protected from developing a disease such as a cancer disease or the disease condition is ameliorated by inducing cytotoxicity.

The particles described herein comprise RNA comprising a cytotoxic nucleotide or cytotoxic nucleotide analog and/or being covalently attached to a cytotoxin. Such RNA is also termed modified toxic immunostimulating RNA (mtiRNA) herein. The particles optionally may further comprise other RNA such as non-mtiRNA, in particular unmodified or non-toxic RNA. For purposes of the present invention the mtiRNA as well as other RNA are commonly referred to as "RNA" herein.

In the context of the present invention, the term "RNA" relates to a molecule which comprises ribonucleotide residues and preferably is entirely or substantially composed of ribonucleotide residues. "Ribonucleotide" relates to a nucleotide with a hydroxyl group at the 2'-position of a β-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

RNA can be isolated from cells, can be made from a DNA template, or can be chemically synthesized using methods known in the art. In preferred embodiments, RNA is synthesized in vitro from a DNA template. In one particularly preferred embodiment, RNA, in particular mRNA, is generated by in vitro transcription from a DNA template. The in vitro transcription methodology is known to the skilled person. For example, there is a variety of in vitro transcription kits commercially available. In one particularly preferred embodiment, RNA is in vitro transcribed RNA (IVT RNA). For providing mtiRNA, cytotoxic nucleotides or cytotoxic nucleotide analogs can be incorporated during synthesis such as chemical synthesis or in vitro transcription, or modifications can be added on the RNA after transcription.

According to the invention, "RNA" includes mRNA, tRNA, rRNA, snRNAs, ssRNA, and dsRNAs.

According to the invention preferred as RNA are synthetic oligonucleotides of 6 to 100, preferably 10 to 50, in particular 15 to 30 or 15 to 20 nucleotides or long transcripts such as messenger RNA (mRNA) of more than 50 nucleotides, preferably of 50 to 10,000, preferably 100 to 5000, in particular 200 to 1000 nucleotides.

According to the present invention, the term "mRNA" means "messenger-RNA" and relates to a "transcript" which may be generated by using a DNA template and may encode a peptide or protein. Typically, an mRNA comprises a 5'-UTR, a protein coding region, and a 3'-UTR. In the context of the present invention, mRNA may be generated by in vitro transcription from a DNA template.

"ssRNA" means single-stranded RNA. ssRNA may contain self-complementary sequences that allow parts of the RNA to fold and pair with itself to form double helices.

According to the invention, "dsRNA" means double-stranded RNA and is RNA with two partially or completely complementary strands. The size of the strands may vary from 6 nucleotides to 10000, preferably 10 to 8000, in particular 200 to 5000, 200 to 2000 or 200 to 1000 nucleotides.

There is no specific ribonucleotide sequence requirement for the RNA molecules to be suitable for preparing particles according to the present invention. However, it is not excluded that certain RNA sequences would provide best biological activities. However, preferably, the RNA component should contain at least 25% uridine residues.

In one embodiment, the RNA has an U content of more than 20%. In particular aspects, the RNA comprises an U content greater than about 25%, greater than about 30%, greater than about 35%, greater than about 40%, and so forth.

As used herein, the term "U content" refers to the amount of nucleosides of a particular RNA molecule or RNA sequence (including mtiRNA) that are uridine (U) typically expressed as a percent. Where the sequence of particular RNA is known, the U content can be determined using the formula:

$$\frac{U}{A+U+G+C} \times 100$$

wherein G, C, A and U refer to the number of each residue in the particular RNA molecule or RNA sequence, to provide a percent U content.

As explained herein, all or a portion such as at least 5%, at least 10%, at least 20%, at least 30%, at least 40%, at least 50%, at least 60%, at least 70%, at least 80%, at least 90%, at least 95%, or at least 98% of the U residues of a mtiRNA may be modified so as to provide the cytotoxic nucleotide or cytotoxic nucleotide analog, for example fluorouridine.

The term "nucleoside" relates to compounds which can be thought of as nucleotides without a phosphate group. While a nucleoside is a nucleobase linked to a sugar (e.g. ribose or deoxyribose), a nucleotide is composed of a nucleoside and one or more phosphate groups. Examples of nucleosides include cytidine, uridine, adenosine, and guanosine.

The five standard nucleosides which make up nucleic acids are uridine, adenosine, thymidine, cytidine and guanosine. The five nucleosides are commonly abbreviated to their one letter codes U, A, T, C and G, respectively. However, thymidine is more commonly written as "dT" ("d" represents "deoxy") as it contains a 2'-deoxyribofuranose moiety rather than the ribofuranose ring found in uridine. This is because thymidine is found in deoxyribonucleic acid (DNA) and not ribonucleic acid (RNA). Conversely, uridine is found in RNA and not DNA. The remaining three nucleosides may be found in both RNA and DNA. In RNA, they would be represented as A, C and G, whereas in DNA they would represented as dA, dC and dG.

The term "cytotoxic nucleotide or cytotoxic nucleotide analog" as used herein refers to any nucleotide or nucleotide analog, in particular nucleotide or nucleotide analog which can be incorporated into nucleic acids such as RNA, which is cytotoxic or comprises a moiety such as a nucleoside or nucleoside analog or nucleobase or nucleobase analog which is cytotoxic. The cytotoxic nucleotide or cytotoxic nucleotide analog may be cytotoxic if part of a nucleic acid molecule, in particular RNA molecule, and/or following release of a cytotoxic moiety such as a nucleoside or nucleoside analog or nucleobase or nucleobase analog. Analogs are similar to natural compounds and moieties, however, they are modified so as to provide certain effects such as cytotoxicity. Accordingly the term "cytotoxic nucleotide or cytotoxic nucleotide analog" includes cytotoxic purine nucleoside analogs and cytotoxic pyrimidine nucleoside analogs such as cytotoxic analogs or homologs of A, G, U, C, dA, dG, dT, dC.

In various embodiments, the modifications of a cytotoxic nucleotide or cytotoxic nucleotide analog to provide cytotoxicity are on the base moiety (e.g. 5-fluoro-uridine (5-FU), 6-mercaptopurine, deoxycoformycin (Pentostatin) and 2-chloro-adenine) or on the sugar moiety (e.g. cytosine arabinoside (cytarabine) or Gemcitabine) or both (e.g. Fludarabine).

In various embodiments, adenine and/or guanine residues are modified in 6-mercaptopurine or deoxycoformycin or fludarabine, adenine residues are modified in 2-chloro-adenine, cytidine residues are modified in cytarabine or gemcitabine and/or uracil residues are modified in fluorouracil such as 5-fluorouracil. In one particularly preferred embodiment, uracil residues are modified in fluorouracil such as 5-fluorouracil.

According to the invention, the term "cytotoxic nucleotide or cytotoxic nucleotide analog" includes, but is not limited to, nucleotide and nucleotide analogs comprising a moiety selected from the group consisting of:

Azacitidine (4-Amino-1-β-D-ribofuranosyl-1,3,5-triazin-2(1H)-one),

Cladribine (5-(6-Amino-2-chloro-purin-9-yl)-2-(hydroxymethyl)oxolan-3-ol),

Clofarabine (5-(6-amino-2-chloro-purin-9-yl)-4-fluoro-2-(hydroxymethyl)oxolan-3-ol), Cytarabine (4-amino-1-[(2R,3S,4R,5R)-3,4-dihydroxy-5-(hydroxymethyl)oxolan-2-yl] pyrimidin-2-one), Decitabine (4-Amino-1-(2-deoxy-β-D-erythro-pentofuranosyl)-1,3,5-triazin-2(1H)-one), Floxuridine (5-Fluoro-1-[4-hydroxy-5-(hydroxymethyl) tetrahydrofuran-2-yl]-1H-pyrimidine-2,4-dione), Fludarabine ([(2R,3R,4S,5R)-5-(6-amino-2-fluoro-purin-9-yl)-3,4-dihydroxy-oxolan-2-yl]methoxyphosphonic acid), Fluorouridine such as 5-fluoro-uridine, Gemcitabine (4-amino-1-(2-deoxy-2,2-difluoro-β-D-erythro-pentofuranosyl)pyrimidin-2(1H)-on), Nelarabine ((2R,3S,4S,5R)-2-(2-amino-6-methoxy-purin-9-yl)-5-(hydroxymethyl)oxolane-3,4-diol), Pentostatin ((R)-3-((2R,4S,5R)-4-hydroxy-5-(hydroxymethyl)tetrahydrofuran-2-yl)-3,6,7,8-tetrahydroimidazo[4,5-d][1,3]diazepin-8-ol), Azathioprine (6-[(1-Methyl-4-nitro-1H-imidazol-5-yl) sulfanyl]-7H-purine), Carmofur (5-fluoro-N-hexyl-2,4-dioxo-pyrimidine-1-carboxamide), Mercaptopurine (3,7-dihydropurine-6-thione), Tegafur ((RS)-5-Fluoro-1-(tetrahydrofuran-2-yl)pyrimidine-2,4(1H,3H)-dione), and Tioguanine (2-amino-1H-purine-6(7H)-thione).

Useful classes of cytotoxic agents (cytotoxins) include, for example, antitubulin agents, DNA minor groove binders (e.g., enediynes and lexitropsins), DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, nitrosoureas, platinols, pre-forming compounds, purine antimetabolites, puromycins, radiation sensitizers, steroids, taxanes (e.g., paclitaxel and docetaxel), topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

Examples of anti-tubulin agents include, but are not limited to, dolastatins (e.g., auristatin E, AFP, MMAF, MMAE, AEB, AEVB), maytansinoids, taxanes (e.g., paclitaxel, docetaxel), T67 (Tularik), vinca alkyloids (e.g., vincristine, vinblastine, vindesine, and vinorelbine), baccatin derivatives, taxane analogs (e.g., epothilone A and B), nocodazole, colchicine and colcimid, estramustine, cryptophysins, cemadotin, combretastatins, discodermolide, and eleutherobin.

In one embodiment, the term "cytotoxin" refers to cytotoxic antibodies. The term "cytotoxic antibody" includes but is not limited to monoclonal antibodies (mABs) having the ability to target diseased cells such as tumor cells, marking them for immune-effector mediated cell killing (complement-dependent cytotoxicity (CDC), antibody-dependent cellular cytotoxicity (ADCC)) and/or leading to reduced proliferation and apoptosis.

The term "cytotoxin" also includes antigen-specific structures such as mABs conjugated to cytotoxic drugs as described herein. By combining the unique targeting capabilities of an antibody with the cancer-killing ability of a cytotoxic drug, antibody-drug conjugates (ADCs) exhibit lower side effects and provide a wider therapeutic window compared to traditional chemotherapeutic agents. In one preferred embodiment, the target antigen (disease-associated antigen) bound by the cytotoxic antibody is localized on the cell surface and accessible to circulating antibody.

According to the invention, the term "antigen-specific structure" includes any compound that has a binding capacity to a target antigen such as a disease-associated antigen. The term includes molecules such as antibodies and antibody fragments, bispecific or multispecific molecules, chimeric antigen receptors (CARs) and all artificial binding molecules (scaffolds) having a binding capacity to the target including but not limited to nanobodies, affibodies, anticalins, DARPins, monobodies, avimers, and microbodies. In one embodiment said binding is a specific binding.

The term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies and chimeric antibodies. Each heavy chain is comprised of a heavy chain variable region (VH) and a heavy chain constant region. Each light chain is comprised of a light chain variable region (VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "RNA covalently attached to a cytotoxin" includes situations where one or more molecules of the same cytotoxin are covalently attached to an RNA molecule as well as where different cytotoxins are covalently attached to an RNA molecule. In the latter situation, one or more molecules of each of the different cytotoxins may be attached to an RNA molecule, or a combination thereof (e.g. one molecule of one cytotoxin is attached while several molecules of another cytotoxin are attached).

The generation of RNA-cytotoxin conjugates can be accomplished by any technique known to the skilled artisan.

RNA-cytotoxin conjugates can be prepared by binding the cytotoxin to RNA in accordance with a conventional technique. RNA and a cytotoxin may be directly bound to each other via their own linker groups or indirectly via a linker or other substance. There are many linking groups known in the art for making RNA-cytotoxin conjugates. A linker preferably comprises one or more functional groups that react with either or both of the RNA and the cytotoxin.

Most preferably, the mtiRNA is an oligonucleotide that has the following sequence (written 5' to 3'): "21mer5FU": A.G.U(5F).G.U(5F).U(5F).A.U(5F).U(5F).C.U(5F).U (5F).G.U(5F).A.U(5F).G.GU(5F). U(5F).G where U(5F) is 5-fluorouridine (SEQ ID NO: 1).

According to the invention, the stability of RNA may be modified as required. For example, RNA may be stabilized by one or more modifications having stabilizing effects on RNA.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

In one embodiment of the invention, the RNA used according to the invention has uncapped 5'-triphosphates (for example on non coding transcript).

The RNA according to the invention may have modified naturally occurring or synthetic ribonucleotides in order to increase its stability. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA.

Of course, if according to the present invention it is desired to decrease stability of RNA, it is possible to modify RNA so as to interfere with the function of elements as described above increasing the stability of RNA.

In one embodiment, the RNA described herein such as mtiRNA is (modified) RNA, in particular (modified) mRNA, encoding a peptide or protein. According to the invention, the term "RNA encoding a peptide or protein" means that the RNA, if present in the appropriate environment, preferably within a cell, can direct the assembly of amino acids to produce, i.e. express, the peptide or protein during the process of translation. Preferably, RNA according to the invention is able to interact with the cellular translation machinery allowing translation of the peptide or protein.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

Particles of the present invention preferably have a defined average size (diameter) of about 10 to about 1000 nm, preferably about 50 nm to about 400 nm, more preferably about 100 nm to about 200 nm.

The average "size" of the particles is generally the "design size" or intended size of the particles prepared according to an established process. Size may be a directly measured dimension, such as average or maximum diameter, or may be determined by an indirect assay such as a filtration screening assay. Direct measurement of particle size is typically carried out by dynamic light scattering. As minor variations in size arise during the manufacturing process, a variation up to 40% of the stated measurement is acceptable and considered to be within the stated size. Alternatively, microcarrier size may be determined by filtration screening assays. For example, a particle preparation is less than a stated size, if at least 97% of the particles pass through a "screen-type" filter of the stated size.

Cationic polymers or lipids contemplated for use as carriers in the particles of the present invention include any substances or vehicles with which RNA, in particular mtiRNA, can be associated, e.g. by forming complexes with the RNA or forming vesicles in which the RNA is enclosed or encapsulated, preferably resulting in increased stability of the RNA compared to naked RNA.

The carriers useful according to the invention include lipid-containing carriers such as cationic lipids, liposomes and micelles, cationic polymers such as DEAE dextran or polyethyleneimine and nanoparticles.

Cationic lipids may form complexes with negatively charged nucleic acids. Any cationic lipid may be used according to the invention. Cationic lipids and cationic polymers can be used to complex nucleic acids, thereby forming so-called lipoplexes (lipids plus RNA), polyplexes (polymer plus RNA), and lipopolyplexes (lipid plus polymer plus RNA), respectively, and these complexes have been shown to deliver nucleic acids into cells.

In one embodiment, the polyplex or lipopolyplex comprises at least one agent selected from the group consisting of an RNA-complexing peptide or protein. In one embodiment, the at least one cationic polymer comprises at least one agent selected from the group consisting of Protamine, polyethyleneimine, a poly-L-lysine, a poly-L-arginine or a histone.

In one embodiment, the lipoplex is a cationic liposome. In one embodiment, the liposome comprises a phospholipid such as phosphatidylcholine and/or a sterol such as cholesterol.

Liposomes are microscopic lipidic vesicles often having one or more bilayers of a vesicle-forming lipid, such as a phospholipid, and are capable of encapsulating a drug. Different types of liposomes may be employed in the context of the present invention, including, without being limited thereto, multilamellar vesicles (MLV), small unilamellar vesicles (SUV), large unilamellar vesicles (LUV), sterically stabilized liposomes (SSL), multivesicular vesicles (MV), and large multivesicular vesicles (LMW) as well as other bilayered forms known in the art. The size and lamellarity of the liposome will depend on the manner of preparation and the selection of the type of vesicles to be used will depend on the preferred mode of administration. Preferred injectable liposomes are those in the size range of 10-500, 20-400, 50-200, 50-150, 50-120, 50-100, or 50-90 nm in diameter. Cationic liposomes are structures that are made of positively charged lipids and are increasingly being used in gene therapy due to their favourable interactions with negatively charged nucleic acids and cell membranes. Cationic liposomes are also known as cationic lipoplexes. Liposomes should not be confused with micelles and reverse micelles composed of monolayers. The lipid assembly may be combined with stabilizers. Non-limiting examples of stabilizers include cholesterol and similar membrane active sterols, lipopolymers such as PEGylated lipids.

Formation of liposomes is not a spontaneous process. Lipid vesicles are formed when phospholipids such as lecithin are placed in water and consequently form one bilayer or a series of bilayers, each separated by water molecules, once enough energy is supplied. Liposomes may be formed using standard methods such as the reverse evaporation method (REV), the dehydration-rehydration method (DRV), sonication or other suitable methods. Liposomes can be created, for example, by sonicating phospholipids in water. Low shear rates create multilamellar liposomes, which have many layers. Continued high-shear sonication tends to form smaller unilamellar liposomes. In this technique, the liposome contents are the same as the contents of the aqueous phase. Sonication is generally considered a "gross" method of preparation as it can damage the structure of the drug to be encapsulated. Newer methods such as extrusion and Mozafari method are employed to produce materials for human use.

After liposome formation, the liposomes can be sized to obtain a population of liposomes having a substantially homogeneous size range, typically between about 10 and 500 nm.

Any suitable liposome-forming material can be used in the present liposomes.

The liposomes can include a vesicle-forming lipid derivatized with a hydrophilic polymer to form a surface coating of hydrophilic polymer chains on the liposome surface.

According to the invention, Protamine is preferred as cationic carrier agent (cationic polymer). The term "Protamine" refers to any of various strongly basic proteins of relatively low molecular weight that are rich in arginine and are found associated especially with DNA in place of somatic histones in the sperm cells of various animals (as fish). In particular, the term "Protamine" refers to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin.

According to the invention, the term "Protamine" as used herein is meant to comprise any Protamine amino acid sequence obtained or derived from native or biological sources including fragments thereof and multimeric forms of said amino acid sequence or fragment thereof. Furthermore, the term encompasses (synthesized) polypeptides which are artificial and specifically designed for specific purposes and isolated from native or biological sources.

The Protamine used according to the present invention can be sulfated Protamine or hydrochloride Protamine. In a preferred embodiment, the Protamine source used for the production of the particles of the invention is Protamine 5000 which contains Protamine at more than 10 mg/ml (5000 heparin-neutralizing units per ml) in an isotonic salt solution and which is diluted as set forth above.

The particles of the invention preferably have a Protamine:RNA weight ratio from 16:1 to 1:2, preferably from 8:1 to 1:2, more preferably from 4:1 to 1:2. In one embodiment, the lower range limit of the Protamine:RNA weight ratio is 1:1, preferably 2:1. The RNA may consist only in mtiRNA or in a mixture of mtiRNA and other RNA such as non-toxic RNA.

In accordance with one embodiment of the invention the particles of the invention comprise on their outer surface a targeting agent or ligand such as an antibody which can selectively or preferably deliver the particles to a target cell population, and/or to a target organ or tissue. For example, liposomes bearing ligands can target receptors expressed on diseased cells. This ligand-binding promotes efficient drug uptake into cells and enhances efficacy. One targeting means which has been explored employs antibodies attached covalently or through electrostatic interactions to particle surfaces.

The ligand may be capable of binding to a disease-associated antigen such that the particles when administered accumulate at a diseased organ or tissue characterized by cells expressing the disease-associated antigen and preferably being characterized by association of the disease-associated antigen with their cell surface, e.g. the disease-associated antigen is a transmembrane protein. The disease-associated antigen may be a tumor-associated antigen and is preferably associated with the surface of a diseased cell such as a tumor cell but preferably not with the surface of a healthy cell. Preferably the ligand for site specific targeting binds to an extracellular portion of the disease-associated antigen.

The term "peptide" according to the invention comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" preferentially refers to large peptides, preferably to peptides with more than 100 amino acid residues, but in general the terms "peptide" and "protein" are synonyms and are used interchangeably herein.

According to the present invention, RNA such as mtiRNA may encode a peptide or protein. Accordingly, RNA may contain a coding region (open reading frame (ORF)) encoding a peptide or protein. For example, RNA may encode and express an antigen or a pharmaceutically active peptide or protein such as an immunologically active compound (which preferably is not an antigen). In this respect, an "open reading frame" or "ORF" is a continuous stretch of codons beginning with a start codon and ending with a stop codon.

The term "pharmaceutically active peptide or protein" includes a peptide or protein that can be used in the treatment of a subject where the expression of a peptide or protein would be of benefit, e.g., in ameliorating the symptoms of a disease or disorder. For example, a pharmaceutically active protein can replace or augment protein expression in a cell which does not normally express a protein or which misexpresses a protein, e.g., a pharmaceutically active protein can compensate for a mutation by supplying a desirable protein. In addition, a "pharmaceutically active peptide or protein" can produce a beneficial outcome in a subject, e.g., can be used to produce a protein to which vaccinates a subject against an infectious disease. Preferably, a "pharmaceutically active peptide or protein" has a positive or advantageous effect on the condition or disease state of a subject when administered to the subject in a therapeutically effective amount. Preferably, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein. The term "pharmaceutically active peptide or protein" includes peptides and proteins that are antigens, i.e., the peptide or protein elicits an immune response in a subject which may be therapeutic or partially or fully protective.

Examples of pharmaceutically active proteins include, but are not limited to, cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthetic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin glucocerebrosidase, erythropoietin granulocyte colony stimulating factor (GCSF) or modified Factor VIII, anticoagulants and the like.

In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin. In one embodiment, the pharmaceutically active protein according to the invention is an interleukin selected from the group consisting of IL-2, IL-7, IL-12, IL-15, and IL-21.

The term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also downregulate other aspects of the immune response, for example shifting the immune response away from a TH2 immune response, which is useful for treating a wide range of TH2 mediated diseases. Immunologically active compounds can be useful as vaccine adjuvants.

In one embodiment, RNA that codes for an antigen such a disease-associated antigen is administered to a mammal, in particular if treating a mammal having a disease involving or expressing the antigen (disease-associated antigen) is desired. The RNA is preferably taken up into the mammal's antigen-presenting cells (monocytes, macrophages, dendritic cells or other cells). An antigenic translation product of the RNA is formed and the product is displayed on the surface of the cells for recognition by T cells. In one embodiment, the antigen or a product produced by optional procession thereof is displayed on the cell surface in the context of MHC molecules for recognition by T cells through their T cell receptor leading to their activation.

Interferons are important cytokines characterized by antiviral, antiproliferative and immunomodulatory activities. Interferons are proteins that alter and regulate the transcription of genes within a cell by binding to interferon receptors on the regulated cell's surface, thereby preventing viral replication within the cells. The interferons can be grouped into two types. IFN-gamma is the sole type II interferon; all others are type I interferons. Type I and type II interferons differ in gene structure (type II interferon genes have three exons; type I, one), chromosome location (in humans, type II is located on chromosome-12; the type I interferon genes are linked and on chromosome-9), and the types of tissues where they are produced (type I interferons are synthesized ubiquitously, type II by lymphocytes). Type I interferons competitively inhibit each others binding to cellular receptors, while type II interferon has a distinct receptor. According to the invention, the term "interferon" or "IFN" preferably relates to type I interferons, in particular IFN-alpha and IFN-beta.

In the context of the present invention the terms "salt(s)" and "electrolyte(s)" are used interchangeably and mean a compound that at least partially dissociates into its respective counter ions in water.

According to the present invention, the term "mM electrolytes" means the concentration in $10^{-3}$ mol per liter of the sum of all electrolytes (including inorganic salts such as NaCl, KCl, $NaH_2PO_4$, $Na_2HPO_4$, $KH_2PO_4$, $K_2HPO_4$, $MgCl_2$, $MnCl_2$, $Na_2SO_4$, $K_2SO_4$, $MgSO_4$ and salts such Tris-HCl, EDTA, Hepes, etc.) in the solutions used to resuspend or to dilute the RNA solutions and in the solutions used to dilute a Protamine stock solutions (such as Protamine 1000 or 5000).

It is demonstrated herein that particles of the present invention have a dual activity: immunostimulation and toxicity on cells such as tumor cells and/or dividing cells. Accordingly, the present invention provides a method of immunochemical treatment of diseases such as cancer comprising the administration of an effective amount of a pharmaceutical composition according to the invention.

The present invention is useful to prime, activate or strengthen the immunity in certain disease states, in particular in the case of chronic diseases, such as cancer or infectious diseases, in particular persistent virus infections as well as to kill diseased cells such as cancer cells or infected cells. Thus, the method of the present invention is useful in the treatment of said disease states.

According to the invention, the term "disease" refers to any pathological state, including cancer diseases. Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor, i.e. a swelling or lesion formed by an abnormal growth of cells (called neoplastic cells or tumor cells), but some, like leukemia, do not. The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

Examples of cancers treatable with the particles and pharmaceutical compositions of the present invention include malignant melanoma, all types of carcinoma (colon, renal cell, bladder, prostate, non-small cell and small cell lung carcinoma, etc.), lymphomas, sarcomas, blastomas, gliomas, etc.

Malignant melanoma is a serious type of skin cancer. It is due to uncontrolled growth of pigment cells, called melanocytes.

According to the invention, a "carcinoma" is a malignant tumor derived from epithelial cells. This group represents the most common cancers, including the common forms of breast, prostate, lung and colon cancer.

Lymphoma and leukemia are malignancies derived from hematopoietic (blood-forming) cells.

A sarcoma is a cancer that arises from transformed cells in one of a number of tissues that develop from embryonic mesoderm. Thus, sarcomas include tumors of bone, cartilage, fat, muscle, vascular, and hematopoietic tissues.

Blastic tumor or blastoma is a tumor (usually malignant) which resembles an immature or embryonic tissue. Many of these tumors are most common in children.

A glioma is a type of tumor that starts in the brain or spine. It is called a glioma because it arises from glial cells. The most common site of gliomas is the brain.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

Particles of the present invention may also be used to treat infectious diseases, particularly when the pathogen would develop in dividing cells or drive cell proliferation. Examples of infectious diseases treatable with the particles and pharmaceutical compositions of the present invention include viral infectious diseases, such as AIDS (HIV), hepatitis A, B or C, herpes, herpes zoster (chicken-pox), German measles (rubella virus), yellow fever, dengue etc. flaviviruses, influenza viruses, hemorrhagic infectious diseases (Marburg or Ebola viruses), bacterial infectious diseases, such as Legionnaire's disease (*Legionella*), gastric ulcer (*Helicobacter*), cholera (*Vibrio*), infections by *E. coli, Staphylococci, Salmonella* or *Streptococci* (tetanus); infections by protozoan pathogens such as malaria, sleeping sickness, leishmaniasis; toxoplasmosis, i.e. infections by *Plasmodium, Trypanosoma, Leishmania* and *Toxoplasma*; or fungal infections, which are caused e.g. by *Cryptococcus neoformans, Histoplasma capsulatum, Coccidioides immitis, Blastomyces dermatitidis* or *Candida albicans*).

The particles and pharmaceutical compositions of the present invention can also be used in conjunction with another therapeutic agent which can be administered prior to, simultaneously with or after administration of the particles or pharmaceutical compositions of the present invention. Such therapeutic agents include chemotherapeutic drugs for cancer patients, e.g. gemcitabine, etopophos, cisplatin, carbo-platin, antiviral agents, anti-parasite agents or anti-bacterial agents and, if administered simultaneously with the particles of the present invention, may be present in a pharmaceutical composition of the present invention.

In particular, the particles and pharmaceutical compositions of the present invention can also be used in conjunction with an immunotherapeutic agent, preferably an immunotherapeutic agent inducing or effecting a targeted, i.e. specific, immune reaction. Such immunotherapeutic agents include agents directed against a disease-associated antigen such as therapeutic antibodies or agents inducing an immune response directed against a disease-associated antigen or cells expressing a disease-associated antigen. Useful immunotherapeutic agents include proteins or peptides inducing a B cell or T cell response against the disease-associated antigen or cells expressing the disease-associated antigen. These proteins or peptides may comprise a sequence essentially corresponding to or being identical to the sequence of the disease-associated antigen or one or more fragments thereof. In one embodiment, the protein or peptide comprises the sequence of an MHC presented peptide derived from the disease-associated antigen. Instead of administering the protein or peptide it is also possible to administer nucleic acid, preferably mRNA, encoding the protein or peptide. The RNA encoding the protein or peptide may be mtiRNA or other RNA contained in particles of the invention. Alternatively or additionally, the RNA encoding the protein or peptide may be RNA not contained in particles of the invention which RNA may be administered simultaneously with (in this case the RNA may form part of a pharmaceutical composition of the invention) and/or prior to and/or after administration of a pharmaceutical composition of the invention. Accordingly, the pharmaceutical composition of the present invention may be used in genetic vaccination, wherein an immune response is stimulated by introduction into a subject a suitable nucleic acid molecule (DNA or mRNA) which codes for an antigen or a fragment thereof.

In one embodiment, a disease-associated antigen is a tumor-associated antigen. In this embodiment, the particles and pharmaceutical compositions of the present invention may be useful in treating cancer or cancer metastasis. Preferably, the diseased organ or tissue is characterized by diseased cells such as cancer cells expressing a disease-associated antigen and/or being characterized by association of a disease-associated antigen with their surface. Immunisation with intact or substantially intact tumor-associated antigen or fragments thereof such as MHC class I and class II peptides or nucleic acids, in particular mRNA, encoding such antigen or fragment makes it possible to elicit a MHC class I and/or a class II type response and thus, stimulate T cells such as CD8+ cytotoxic T lymphocytes which are capable of lysing cancer cells and/or CD4+ T cells. Such immunization may also elicit a humoral immune response (B cell response) resulting in the production of antibodies against the tumor-associated antigen. Furthermore, antigen presenting cells (APC) such as dendritic cells (DCs) can be loaded with MHC class I—presented peptides directly or by transfection with nucleic acids encoding tumor antigens or tumor antigen peptides in vitro and administered to a patient.

According to the present invention, a tumor-associated antigen preferably comprises any antigen which is characteristic for tumors or cancers as well as for tumor or cancer cells with respect to type and/or expression level. In one embodiment, the term "tumor-associated antigen" relates to proteins that are under normal conditions, i.e. in a healthy subject, specifically expressed in a limited number of organs and/or tissues or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2 or 1. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably associated with the cell surface of a cancer cell and is preferably not or only rarely expressed in normal tissues. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. In one embodiment, the amino acid sequence of the tumor-associated antigen is identical between the tumor-associated antigen which is expressed in normal tissues and the tumor-associated antigen which is expressed in cancer tissues. Preferably, a tumor-associated antigen is presented in the context of MHC molecules by a cancer cell in which it is expressed.

Examples for differentiation antigens which ideally fulfill the criteria for tumor-associated antigens as contemplated by the present invention as target structures in tumor immunotherapy, in particular, in tumor vaccination are the cell surface proteins of the claudin family, such as CLDN6 and CLDN18.2. These differentiation antigens are expressed in tumors of various origins, and are particularly suited as target structures in connection with antibody-mediated cancer immunotherapy due to their selective expression (no expression in a toxicity relevant normal tissue) and localization to the plasma membrane.

Further examples for antigens that may be useful in the present invention are p53, ART-4, BAGE, beta-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

The pharmaceutical composition of the present invention may take the form of a vaccine preparation comprising the particles of the invention and at least one antigen such as an antigen as discussed above or an immunogenic fragment thereof, or a nucleic acid, in particular RNA, encoding said antigen or fragment. This RNA may be present within particles of the invention and may optionally be mtiRNA.

An "antigen" is to be understood as meaning any structure which can cause the formation of antibodies and/or the activation of a cellular immune response.

Examples of antigens are polypeptides, proteins, cells, cell extracts, carbohydrates/polysaccharides, polysaccharide conjugates, lipids, and glycolipids. These antigens may be tumor antigens or viral, bacterial, fungal and protozoological antigens or allergens. The term "antigen" also includes derivatized antigens as secondary substance which becomes antigenic—and sensitizing—only through transformation (e.g., intermediately in the molecule, by completion with body protein), and conjugated antigens which, through artificial incorporation of atomic groups (e.g., isocyanates, diazonium salts), display a new constitutive specificity. The antigen may be present in the vaccine according to the invention in the form of a hapten coupled to a suitable carrier. Suitable carriers are known to those ordinarily skilled in the art and include e.g. human serum albumin (HSA), polyethylene glycols (PEG). The hapten may be coupled to the carrier by processes well-known in the prior art, e.g. in the case of a polypeptide carrier via an amide bond to a Lys residue.

The particles of the present invention may be coated by polyethylene glycols thereby enhancing stability or bioavailability or functionality.

By "treat" is meant to administer a compound or composition as described herein to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

The term "immunotherapy" relates to a treatment preferably involving a specific immune reaction and/or immune effector function(s).

The term "immunization" or "vaccination" describes the process of treating a subject for therapeutic or prophylactic reasons.

The term "subject" relates to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "subject" as used herein also includes humans.

The pharmaceutical compositions of the invention are preferably sterile and contain an effective amount of the particles of the invention and optionally of further agents as discussed herein such as therapeutic agents and antigens to generate the desired reaction or the desired effect.

The pharmaceutical compositions of the invention may also comprise an additional immunomodulating agent such as anti-CTL-A4 or anti-PD1 or anti-PDL1 or anti-regulatory T-cell reagents such as an anti-CD25 antibody or cyclophosphamide.

The pharmaceutical compositions of the invention may be administered together with supplementing immunity-enhancing substances such as one or more adjuvants and may comprise one or more immunity-enhancing substances to further increase its effectiveness, preferably to achieve a synergistic effect of immunostimulation.

The term "adjuvant" relates to compounds which prolong or enhance or accelerate an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Because of the presence of the immunostimulating agent according to the invention comprising RNA as the primary immunostimulants, however, only a relatively small amount of CpG DNA is necessary (compared with immunostimulation with only CpG DNA). Thus, CpG DNA could be added to the mtiRNA before addition of for example cationic polymer such as Protamine or cationic lipids so that all nucleic acids are condensed within particles or added on preformed particles. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, INFα, INF-γ, GM-CSF, LT-α, or growth factors, e.g. hGH. Lipopeptides, such as Pam3Cys, are also suitable for use as adjuvants in the pharmaceutical compositions of the present invention.

Pharmaceutical compositions are usually provided in a uniform dosage form and may be prepared in a manner known per se. The pharmaceutical compositions of the invention may e.g. be in the form of a solution or suspension.

The pharmaceutical compositions of the invention may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Suitable preservatives for use in the pharmaceutical compositions of the invention include benzalkonium chloride, chlorobutanol, paraben and thimerosal.

An injectible formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition of the present invention and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly. It can also be intra-tumoral.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution or Glucose 5%. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The following examples are intended to illustrate preferred embodiments of the invention and should not be interpreted to limit the scope of the invention as defined in the claims.

EXAMPLES

Example 1

Method for the Preparation of Particles Containing mtiRNA

A mtiRNA oligoribonucleotide of approximately 21 residues with the sequence 5' A.G.U(5F).G.U(5F).U(5F).A.U (5F).U(5F).C.U(5F).U(5F).G.U(5F).A.U(5F).G.G.U(5F). U(5F).G 3' where U(5F) is 5 fluoro Uridine is synthesized and purified. The product is then lyophilized and resuspended at 0.5 mg/ml in pure water. Protamine IPEX 5000 is diluted 28 times in pure water to provide a solution of Protamine at approximately 0.5 mg/ml in low salt. Equal volumes of RNA and Protamine are mixed together. Immediate and intensive mixing is performed for example by pipeting up and down or by vortexing. The formulation is left for a few minutes on the bench and can then be further diluted with injection solution (for example 5% Glucose). Particles of approximately 100 nm can be detected using a light scattering spectroscopy (FIG. 1). Should the Protamine/mtiRNA particle solution be too diluted, the particles can be recovered by centrifugation or freeze drying and be resuspended in the adequate volume of desired solution before being used for treatment formulation.

Example 2

Particles Containing mtiRNA are at the Same Time Immunostimulating and Toxic to Tumor Cells A mtiRNA oligoribonucleotide of approximately 21 residues with the sequence 5' A.G.U(5F).G.U(5F).U(5F).A.U (5F).U(5F).C.U(5F).U(5F).G.U(5F).A.U(5F).G.G.U(5F). U(5F).G 3' where U(5F) is 5 fluoro Uridine is synthesized and purified. The product is then lyophilized and resuspended at 0.5 mg/ml in pure water. Protamine IPEX 5000 is diluted 28 times in pure water to provide a solution of Protamine at approximately 0.5 mg/ml in low salt. Equal volumes of RNA and Protamine are mixed together.

Immediate and intensive mixing is performed for example by pipeting up and down or by vortexing. The formulation is left for a few minutes on the bench and can then be further diluted with injection solution (for example 5% Glucose). Particles pulsed for a few hours on tumor calls in vitro induce an inhibition of cell growth (FIG. 2) while the same particles incubated with fresh human PBMCs or injected intravenously in animals induce immunostimulation (production of alpha interferon: FIGS. 3 and 4).

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. Furthermore, the teachings and disclosures of all references cited herein are expressly incorporated in their entireties by reference.

The invention claimed is:

1. A particle comprising single stranded RNA (ssRNA), in which the ssRNA is associated with a cationic polymer or lipid or with both a cationic polymer and lipid,
wherein the ssRNA comprises at least 20% modified U residues, wherein each modified U residue is a cytotoxic nucleotide or cytotoxic nucleotide analog.

2. The particle of claim 1, wherein the cytotoxic nucleotide or cytotoxic nucleotide analog is 5 fluoro uridine (5FU).

3. The particle of claim 1, wherein the ssRNA is an oligonucleotide or is a messenger RNA.

4. The particle of claim 1, wherein the cationic polymer is selected from the group consisting of Protamine, polyethyleneimine, poly-L-lysine, poly-L-arginine and histone.

5. The particle of claim 4, wherein the particle comprises ssRNA and Protamine.

6. The particle of claim 5, wherein the Protamine-ssRNA particle is a Protamine-ssRNA nanoparticle having a size in the range from about 10 nm to about 990 nm.

7. The particle of claim 6, wherein the Protamine-sRNA nanoparticle has a Protamine:ssRNA mass ratio in the range from about 16:1 to about 1:2.

8. A pharmaceutical composition comprising the particle of claim 1, and a pharmaceutically acceptable carrier.

9. The pharmaceutical composition of claim 8, further comprising an antigen and/or an adjuvant.

10. A method for treating cancer, comprising administering to a subject having cancer an amount effective of the particle of claim 1 to induce an immune response and induce cytotoxicity, thereby treating the cancer.

11. The particle of claim 1, wherein the sRNA is an oligonucleotide or is a messenger RNA, and wherein the cationic polymer is Protamine.

12. The method of claim 10, wherein each cytotoxic nucleotide or cytotoxic nucleotide analog is 5 fluoro uridine (5FU).

13. The method of claim 11, wherein each cytotoxic nucleotide or cytotoxic nucleotide analog is 5 fluoro uridine (5FU).

* * * * *

UNITED STATES PATENT AND TRADEMARK OFFICE
CERTIFICATE OF CORRECTION

PATENT NO. : 10,980,875 B2
APPLICATION NO. : 15/763541
DATED : April 20, 2021
INVENTOR(S) : Steve Pascolo It is certified that error appears in the above-identified patent and that said Letters Patent is hereby corrected as shown below:

On the Title Page

Column 1, "(73) Assignee: BIONTECH AG, Mainz (DE)" should be "(73) Assignee: BIONTECH SE, Mainz (DE)"

Signed and Sealed this
Fifteenth Day of November, 2022

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 21
<212> TYPE: RNA
<213> ORGANISM: Artificial Sequence
<220> FEATURE:
<223> OTHER INFORMATION: mtiRNA
<220> FEATURE:
<221> NAME/KEY: misc_feature
<222> LOCATION: (3)..(3)
<223> OTHER INFORMATION: 5-fluorouridine
<220> FEATURE:
```

```
<221> NAME/KEY: misc_feature
<222> LOCATION: (5)..(5)
<223> OTHER INFORMATION: 5-fluorouridine
<220> FEATURE:
<221> NAME/KEY: misc_feature
<222> LOCATION: (6)..(6)
<223> OTHER INFORMATION: 5-fluorouridine
<220> FEATURE:
<221> NAME/KEY: misc_feature
<222> LOCATION: (8)..(8)
<223> OTHER INFORMATION: 5-fluorouridine
<220> FEATURE:
<221> NAME/KEY: misc_feature
<222> LOCATION: (9)..(9)
<223> OTHER INFORMATION: 5-fluorouridine
<220> FEATURE:
<221> NAME/KEY: misc_feature
<222> LOCATION: (11)..(11)
<223> OTHER INFORMATION: 5-fluorouridine
<220> FEATURE:
<221> NAME/KEY: misc_feature
<222> LOCATION: (12)..(12)
<223> OTHER INFORMATION: 5-fluorouridine
<220> FEATURE:
<221> NAME/KEY: misc_feature
<222> LOCATION: (14)..(14)
<223> OTHER INFORMATION: 5-fluorouridine
<220> FEATURE:
<221> NAME/KEY: misc_feature
<222> LOCATION: (16)..(16)
<223> OTHER INFORMATION: 5-fluorouridine
<220> FEATURE:
<221> NAME/KEY: misc_feature
<222> LOCATION: (19)..(19)
<223> OTHER INFORMATION: 5-fluorouridine
<220> FEATURE:
<221> NAME/KEY: misc_feature
<222> LOCATION: (20)..(20)
<223> OTHER INFORMATION: 5-fluorouridine

<400> SEQUENCE: 1
aguguuauuc uuguaugguu g                                                    21
```